US00PP24916P2

(12) United States Plant Patent
Bergman

(10) Patent No.: US PP24,916 P2
(45) Date of Patent: Sep. 23, 2014

(54) ***CHRYSANTHEMUM* PLANT NAMED 'CIDZ0045'**

(50) Latin Name: *Chrysanthemum×morifolium*
Varietal Denomination: CIDZ0045

(71) Applicant: Syngenta Crop Protection AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 80 days.

(21) Appl. No.: 13/694,456

(22) Filed: Dec. 4, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — Joshua L. Price

(57) ABSTRACT

A new *Chrysanthemum* plant named 'CIDZ0045' particularly distinguished by the large yellow decorative-type inflorescences, strong stems with glossy foliage with an 8 week blackcloth flowering response time.

1 Drawing Sheet

Latin name of the genus and species of the plant claimed: *Chrysanthemum×morifolium.*

Varietal denomination: 'CIDZ0045'.

BACKGROUND OF THE NEW PLANT

The present invention comprises a new *Chrysanthemum*, botanically known as *Chrysanthemum×morifolium,* and hereinafter referred to by the variety name 'CIDZ0045'.

'CIDZ0045' is a product of a planned breeding program. The new cultivar has large yellow decorative-type inflorescences, strong stems with glossy foliage with an 8 week blackcloth flowering response time.

'CIDZ0045' originates as a whole plant mutation of 'Synhoney Durango', U.S. Plant Pat. No. 22,155. 'CIDZ0045' was discovered and selected by the inventor as a single flowering plant within a large population of the parent cultivar, grown in pots outdoors under a shade structure in Fort Myers, Fla. in November 2009. The parent cultivar 'Synhoney Durango' has ray floret petals that are a deeper hued golden yellow with a reddish base, narrower petals, and less reflexing apices.

The first act of asexual reproduction of 'CIDZ0045' was accomplished when vegetative cuttings were propagated from the initial selection in January 2010 in a greenhouse in Fort Myers, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIDZ0045' are firmly fixed and are retained through successive generations of asexual reproduction.

'CIDZ0045' has not been observed under all possible environmental conditions. The phenotype may vary significantly with variations in environment such as temperature, light intensity, and day length.

A Plant Breeder's Right for this cultivar was applied for in Canada on Jun. 29, 2012 (12-7649). 'CIDZ0045' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0045' with colors being as true as possible with an illustration of this type. The photographic drawing shows 4 flowering plants of the new variety growing in 1 container and a close-up of the inflorescences.

DETAILED BOTANICAL DESCRIPTION

The plant descriptions, measurements and aforementioned photographs were taken in Gilroy, Calif. in early October 2012 under natural light. These plants were grown 4 plants in a 6-inch container in a greenhouse in Nipomo, Calif. These plants used in the photograph and descriptions were about 10-12 weeks old.

Color references are made to The Royal Horticultural Society Colour Chart (R.H.S.) 2001.

TABLE 1

DIFFERENCES BETWEEN THE NEW VARIETY 'CIDZ0045' AND A MOST SIMILAR VARIETY

| | 'CIDZ0045' | 'Yocovington' (U.S. Plant Pat. No. 13,031) |
|---|---|---|
| Inflorescence size: | Larger | Smaller |
| Inflorescence type in low light conditions: | No changes | More open center flowering |
| Blackcloth flowering response: | 4-5 days slower | 4-5 days faster |

Plant:

*Form, growth and habit*.—Herbaceous pot-type, stems upright, freely branching, strong and moderately vigorous growth habit.

*Plant height*.—20-22.0 cm.

*Plant height* (*inflorescence included*).—27-30.0 cm.

*Plant width*.—20.0 cm.

Roots:

*Number of days to initiate roots*.—About 4 days at about 22 degrees C.

*Number of days to produce a rooted cutting*.—4-6 days at 22 degrees C.

*Type*.—Fine, fibrous, free branching.

*Color*.—RHS N155B but whiter.

Foliage:

*Arrangement*.—Alternate.

*Immature, leaf color, upper surface*.—Closest to RHS 147A but slightly darker.

*Immature, leaft color, lower surface*.—Closest to RHS 147B.

*Mature, leaf color, upper surface*.—Closest to RHS 147A but more green.

*Mature, leaft color, lower surface*.—Closest to RHS 147B but more green.

*Length*.—8.5-9.3 cm.

*Width*.—5.5-6.0 cm.

*Shape*.—Ovate.

*Base shape*.—Attenuate.

*Apex shape*.—Mucronulate.

*Margin*.—Palmately lobed; slightly dentate.

*Texture, upper surface*.—Bifid T-shaped hairs.

*Texture, lower surface*.—Bifid T-shaped hairs.

*Color of veins, upper surface*.—RHS 144B.

*Color of veins, lower surface*.—RHS 144B.

*Pattern of veining*.—Palmate.

*Petiole color*.—RHS 144B.

*Length*.—2-2.4 cm.

*Diameter*.—0.4 cm.

*Texture*.–Bifid T-shaped hairs.

Stem:

*Quantity of main branches per plant*.—3-5.

*Color of stem*.—RHS 137A but appears lighter due to hairs.

*Length of stem*.—1.8-2.1 cm.

*Diameter*.—0.5 cm.

*Length of internodes*.—0.5-1.0 cm.

*Texture*.—Bifid T-shaped hairs.

*Color of peduncle*.—RHS 137A but appears lighter due to hairs.

*Length of peduncle*.—5-6.0 cm.

*Peduncle diameter*.—0.35 cm.

*Texture*.—Bifid T-shaped hairs.

Inflorescence:

*Type*.—Compositae, solitary decorative-type inflorescences borne terminally above foliage, ray florets arranged acropetally on a capitulum.

*Quantity of short days to flowering* (*response time*).—8 weeks.

*Natural season flowering*.—Not determined on this variety.

*Quantity of inflorescences per plant*.—2-5.

*Lastingness of individual blooms on the plant*.—About 4 weeks depending on temperatures.

*Fragrance*.—Slightly spicy.

Bud (just when opening/showing color):

*Color*.—RHS 1B basally becoming more RHS 6A at the apex.

*Length*.—1.5-2.0 cm.

*Width*.—1.7-1.9 cm.

*Shape*.—Broadly oblate.

Immature inflorescence:

*Diameter*.—8.5 cm.

*Color of ray florets, upper surface*.—Closest to RHS 6A but much brighter.

*Color of ray florets, lower surface*.—RHS 6B but lighter.

Mature inflorescence:

*Diameter*.—13-13.5 cm.

*Depth*.—3.5-4.5 cm.

*Total diameter of disc*.—None showing at this time.

*Receptacle color*.—RHS 145B.

*Receptacle height*.—0.7 cm.

*Receptacle diameter*.—1.3-1.4 cm.

Ray florets:

*Average quantity of florets*.—About 150 in numerous whorls.

*Color of florets, upper surface*.—Closest to RHS 6B.

*Color of florets, lower surface*.—Closest to RHS 3B.

*Length*.—5.3-6.4 cm.

*Width*.—1.5-1.8 cm.

*Shape*.—Oblong to elliptical.

*Apex shape*.—Slightly retuse.

*Base shape*.—Cuneate.

*Margin*.—Entire.

*Texture, upper surface*.—Papillose.

*Texture, lower surface*.—Papillose.

Disc florets:

*Average quantity of florets*.—About 15.

*Color of florets*.—RHS 155C with RHS 17C apex.

*Length*.—0.4-0.5 cm.

*Width*.—0.1 cm.

*Shape*.—Tubular, elongated.

*Apex shape*.—Acute, 5 pointed.

*Texture, inner surface*.—Glabrous.

*Texture, outer surface*.—Glabrous.

Phyllaries:

*Quantity*.—About 25-30.

*Color, upper surface*.—RHS 137B.

*Color, lower surface*.—RHS 137A with some having slight darker blotches.

*Length*.—1-1.5 cm.

*Width*.—0.3-0.4 cm.

*Shape*.—Lanceolate.

*Apex shape*.—Acute.

*Base*.—Fused.

*Margins*.—Entire.

*Texture, upper surface*.—Glabrous.

*Texture, lower surface*.—Bifid T-shaped hairs.

Reproductive organs:

*Pistil*.—1, found on both types of florets. Description here is of those found in the ray florets as those in the disc florets are immature as yet.

*Length*.—0.6 cm.

*Style color*.—RHS 1B to RHS 1C.

*Style length*.—0.5 cm.

*Stigma color*.—RHS 9B.

*Stigma shape*.—Bi-parted.

*Ovary color*.—RHS 145A.

*Ovary length*.—0.1 cm.

*Ovary width*.—0.1 cm.

*Stamens*.—4, found on only on the disc florets.

*Color of filaments*.—RHS 155C.
*Length filaments*.—0.3-0.4 cm.
*Anther color*.—RHS 16A.
*Anther length*.—0.2 cm.
*Anther shape*.—Oblong.
*Color of pollen*.—RHS 17B.
*Pollen amount*.—Good.
*Fertility/seed set*.—Has not been observed to date.
*Disease/pest resistance*.—Has not been observed to date.

What is claimed is:

1. A new and distinct variety of *Chrysanthemum* plant named 'CIDZ0045' substantially as illustrated and described herein.

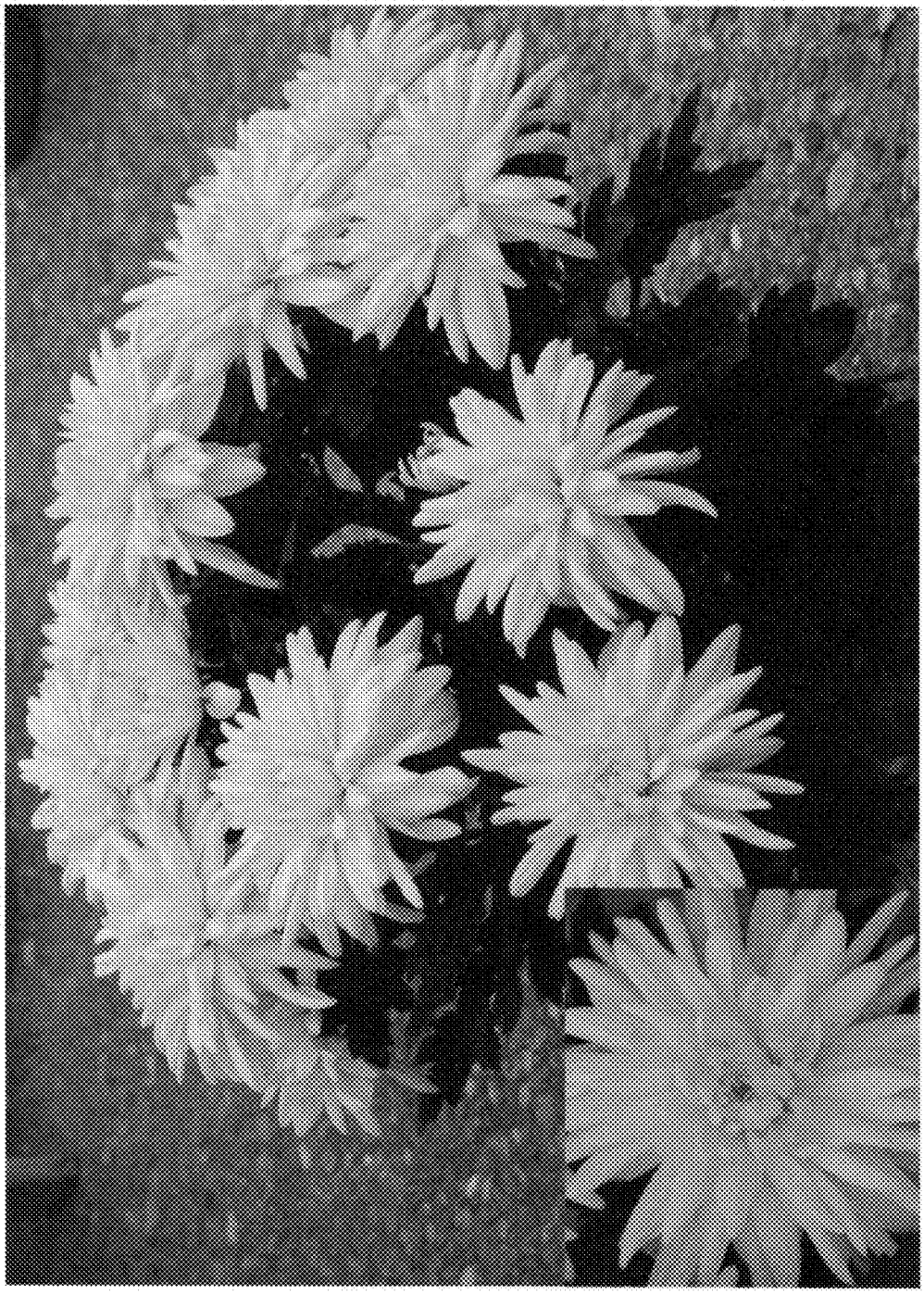

* * * * *